United States Patent [19]
Lohner et al.

[11] Patent Number: 5,719,121
[45] Date of Patent: Feb. 17, 1998

[54] USE OF BALHIMYCIN AS PRODUCTION PROMOTER IN ANIMALS, AND PRODUCTION PROMOTER COMPOSITIONS

[75] Inventors: Manfred Lohner, Eltville; Stefan Scheuermann, Villmar; Laszló Vértesy, Eppstein, all of Germany

[73] Assignee: Hoechst Aktiengesellschaft, Frankfurt am Main, Germany

[21] Appl. No.: 673,220

[22] Filed: Jun. 27, 1996

[30] Foreign Application Priority Data

Jun. 28, 1995 [DE] Germany ............ 195 23 394.8

[51] Int. Cl.⁶ .......... A61K 38/16; A61K 38/00; A01N 37/18; C07K 5/00
[52] U.S. Cl. .......... 514/8; 514/2; 514/9; 514/12; 514/13; 530/317; 530/324; 530/325; 530/326; 530/322; 530/323
[58] Field of Search .......... 514/8, 12, 2, 13, 514/9; 530/324, 325, 326, 317, 322, 323

[56] References Cited

U.S. PATENT DOCUMENTS

| | | | |
|---|---|---|---|
| 3,928,571 | 12/1975 | Raun | 424/118 |
| 5,451,570 | 9/1995 | Nadkarni et al. | 514/8 |

FOREIGN PATENT DOCUMENTS

| | | |
|---|---|---|
| 2072725 | 12/1992 | Canada. |
| 0 468 504 A1 | 1/1992 | European Pat. Off.. |
| 0468504 | 1/1992 | European Pat. Off.. |
| 0 521 408 A1 | 1/1993 | European Pat. Off.. |
| 0521408 | 1/1993 | Germany. |
| 42 26 102 A1 | 2/1994 | Germany. |
| 162280 | 4/1988 | India. |

OTHER PUBLICATIONS

Registry Listing Balhimycin and Derivatives, Registry Numbers 140932-79-2, 82198-76-3, 149250-73-7, 158111-85-4, 148925-35-3, 1997.

Chatterjee, et al., Balhimycin, a New Glycopeptide Antibiotic with an Unusual Hydrated 3-Amino-4-oxoaldopyranose Sugar Moiety, J. Org. Chem., 59 (12), pp. 3480-3484, Jun. 17, 1994.

Nadkarni, et la., Balhimycin, A New Glycopeptide Antibiotic Produced by Amycolatopsis sp. Y-86.21022, J. of Antibiotics, vol. 47, No. 3, pp. 334-341, Mar. 1994.

Derwent Abstract No. 94-049829/07, Aug. 7, 1992.

Nadkarni et al.; Balhimycin, A New Glycopeptide Antibiotic Produced By *Amycolatopsis* sp. Y-86, 21022 Taxonomy, Production, Isolation and Biological Activity; Journal of Antibiotics 47(3) Mar. 1994 334-341.

Primary Examiner—Cecilia J. Tsang
Assistant Examiner—Jennifer Harle
Attorney, Agent, or Firm—Finnegan, Henderson, Farabow, Garrett & Dunner, L.L.P.

[57] ABSTRACT

Balhimycin, where appropriate in combination with one or more of its derivatives, is suitable for promoting production in monogastric or polygastric animals.

18 Claims, No Drawings

USE OF BALHIMYCIN AS PRODUCTION PROMOTER IN ANIMALS, AND PRODUCTION PROMOTER COMPOSITIONS

The present invention relates to the use of balhimycin for promoting production in animals, and to production promoter compositions.

BACKGROUND OF THE INVENTION

Balhimycin, a compound of the formula I

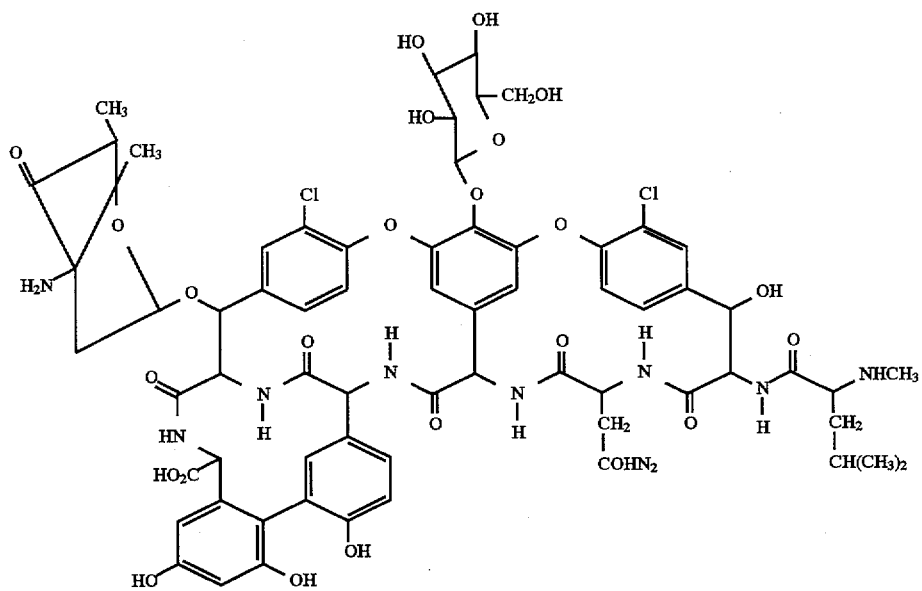

is a known glycopeptide antibiotic (cf. EP 0 468 504 (U.S. Pat. No. 5,451,570)). Derivatives of balhimycin, and their suitability as production promoters in agriculture, have likewise been disclosed (cf. EP 0 521 408). However, the particularly pronounced suitability of balhimycin for promoting production in animals is also surprising with reference to the state of the art.

SUMMARY OF THE INVENTION

The invention consequently relates to the use of balhimycin, where appropriate in combination with one or more of its derivatives, for promoting production in monogastric or polygastric animals, and to compositions for promoting production in monogastric or polygastric animals, which compositions contain balhimycin, where appropriate in combination with one or more of its derivatives.

Balhimycin can be prepared by fermentation of the microorganism Actinomycete sp. DSM 5908 as described in the above-mentioned EP 0 468 504 (U.S. Pat. No. 5,451,570).

As has been stated, the novel compositions may contain one or more balhimycin derivatives in addition to the balhimycin. These balhimycin derivatives are, in particular, demethylbalhimycin, demethylleucylbalhimycin, deglucobalhimycin, ureidobalhimycin, demethyldeglucobalhimycin, methylbalhimycin, balhimycin R or balhimycin V, and their hydrates and/or physiologically tolerated salts. The preparation and properties of these balhimycin derivatives are described in EP 0 521 408 (U.S. Ser. Nos. 07/907,747 and 08/475,642) which is expressly incorporated herein by reference.

The active agent of the novel compositions comprises from 50 to 100%, preferably from 60 to 100%, in particular from 70 to 100%, by weight, of balhimycin.

The novel compositions are of particular importance when used for male and female economically useful agricultural animals, such as poultry, piglets, fattening pigs, breeding pigs, calves, fattening cattle and dairy cows. The novel compositions can also be used for promoting production in castrated animals. The compositions are also suitable for promoting production in other animals such as rabbits or fish. That which is very particularly preferred is the use of the novel compositions for poultry, piglets and fattening pigs, in particular for broilers and fattening turkeys.

In the context of this invention, production promotion is understood to mean, in particular, an improvement in feed utilization, an increase in live weight gain, an increase in milk production or an increase in egg production by the animal treated with the novel compositions of the invention.

In the context of this invention, the term active agent is understood to mean, balhimycin alone or in combination with one or more of its derivatives.

The active agent is preferably administered to the animals in a dose of from 0.1 to 600 mg per kg of bodyweight per day. The active agent can be administered to the animals in a variety of ways.

The novel compositions differ in their constitution and administration form.

Physiologically tolerated salts and esters of balhimycin and its derivatives, or a combination thereof, for example, are, in accordance with the invention, suitable in place of, or together with, balhimycin and, where appropriate, its derivatives.

It is, for example, possible to add the active agent to the complete feed or supplementary feed, or else to a part of the daily ration. The active agent can be used as a pure substance or as a crude product, for example after extracting the culture broth which contains the active agent, or in a suitable preparation. The feed can be in liquid or solid form. Alternatively, the active agent, the active agent combination or an active agent preparation can be added to the drinking water. It is also possible to use customary adjuvants, e.g., physiologically tolerated carriers, to bring the active agent or the active agents into a solid or liquid pharmaceutical preparation for oral administration and to administer active agent or agents, or add active agent or agents to the feed, as such a preparation. It is also possible to administer the active agent or agents parenterally using an implant.

A particularly preferred form of the compositions containing balhimycin and, where appropriate, one or more of its derivatives can be obtained by preparing balhimycin by fermenting a suitable microorganism (cf. EP 0 468 504 (U.S. Pat. No. 5,451,570)) and subjecting the balhimycin, together with non-volatile constituents in the culture broth, to further processing. The disclosure of U.S. Pat. No. 5,451,570 to Nadkarni et al. issued Sep. 19, 1995, is incorporated herein by reference. The balhimycin, together with non-volatile constituents in the culture broth, are isolated, for example, by spray-drying the culture broth containing the balhimycin. This results in a product being obtained which can, depending on the microorganism, contain defined quantities of balhimycin derivatives in addition to the balhimycin. In addition to this, the active agent content of corresponding products can be altered in a specific manner by adding pure balhimycin or one or more of its derivatives to obtain a desired content of the active agent or agents.

A form of administration which is preferred in many cases is that of adding the active agent to the feed in the form of a concentrate (premix). The concentrate can be prepared, for example, by mixing the active agent or the active agent combination, the crude product or the extract which contains the active agent with a physiologically tolerated, solid or liquid excipient or carrier.

Examples of suitable solid excipients or carriers are cereal byproducts, such as wheat middlings, wheat bran or de-oiled rice bran, and also corn meal, soyabean flour, kaolin or calcium carbonate. Liquid excipients or carriers which may be used are physiological salt solutions, water and physiologically tolerated organic solvents. It is possible in this context to use suitable additives, such as emulsifiers, dispersants, suspending agents, wetting agents or gelling agents. As a rule, the concentrate (premix) contains from 0.1 to 20% by weight, preferably from 0.5 to 15% by weight, of the active agent or combination, with it being possible to exceed or fall short of the active agent concentration, depending on the intended use.

When the active agent is administered together with feedstuffs, the expedient procedure is to mix a concentrate homogeneously with the feed. Suitable feedstuffs are those feedstuffs which are customarily used, such as different cereals, offals from oil recovery (e.g. coarse soyabean extraction meal) and other energy-rich and protein-rich substances, such as tapioca and fishmeal, and feed mixtures, supplementary feedstuffs and mineral mixtures prepared therefrom.

As a rule, the optimum increase in growth depends on the composition of the feed, in particular the protein content, and on the content of balhimycin and/or its derivatives or the combination thereof, with a maximum for the increase in growth as a rule being passed through as the active agent content is increased. The optimal dosage can be readily ascertained, in a relatively small number of preliminary experiments, by means of a factorial experimental design. As a rule, the concentration of the active agent in the feed is from 0.1 to 500 mg/kg, preferably from 0.1 to 200 mg/kg, in particular from 0.1 to 100 mg/kg.

The active agent can also be administered in solution or suspension in the drinking water or other drenches, for example in the milk replacer.

The active agent can also be administered such that it is administered, in the form of its solid or liquid pharmaceutical preparation, per os directly to the animals, preferably during, or a short time before or after feeding. When used in this way, the pharmaceutical preparation or composition can, for example, be a tablet, capsule, paste, granular composition, powder, bolus, slow-release bolus, juice, syrup, salt lick or a premix concentrate as described above. This form of administration can be of particular interest especially in the case of grazing animals.

The same auxiliary substances and additives (i.e., physiologically tolerated carriers) can be used for the administration in the form of tablets, capsules, pastes, boli, pills, granules, juices, syrups and the like as are known in pharmaceutical technology, in particular auxiliary substances for preparations for long-term administration with continuous release of the active agent. Preparations of the latter kind which have been specially developed for ruminants are of particular interest. The active agent can, for example, be mixed with pulverulent diluents, such as microcrystalline cellulose, sugar or starch, in order to fill the capsule volume. The tablets can likewise be prepared in a customary manner with the addition of substances such as cellulose, lactose, sodium chloride, starch, dextrin, cellulose derivatives, etc. The auxiliary substances which are customary in pharmacy, such as vegetable oils, Kollidon, cellulose derivatives and the like, can also be used for preparing liquid preparations. An aqueous solution or suspension of balhimycin and/or its analogs can, for example, also contain subsidiary constituents from the crude extract of the culture broth as well as, for example, suitable buffering substances, in addition to the active agent. Preferably, each administration unit should contain from 0.1 to 600 mg of active agent or active agent mixture.

When the active agent or the active agent combination is administered parenterally, the active agents are preferably released continuously in the required dose over an extended period, e.g., some weeks or months, depending on the animal species, using an implant which is prepared and employed in the customary manner known to those of ordinary skill in the art.

In order to improve the effect, combinations with other additives such as antibiotics and chemotherapeutics are also possible.

The active agents, preferably balhimycin, which are employed in accordance with the invention have a positive effect on production. In addition to this, when the supply is being matched to demand, i.e., when the animal can consume as much food as desired, a lower quantity of feed is required, as a rule, for the same weight gain as compared with that required in the absence of the active agent or combination thereof.

As a result, a protein-sparing and feed-sparing effect can be observed. As a rule, this also reduces pollution of the environment by the excreta of the animals.

The following example and demonstrations of activity, and also the content of the appended claims, are intended to illustrate the present invention in more detail but should not be construed to limit the invention.

EXAMPLE

A feeding experiment with balhimycin was carried out in floor management using 160 broilers (80 males and 80 females) which were divided into 5 groups:

1st group: untreated control

2nd group: balhimycin, 15 mg/kg of feed

3rd group: balhimycin, 30 mg/kg of feed

4th group: balhimycin, 45 mg/kg of feed

5th group: balhimycin, 60 mg/kg of feed

The feed had the following composition (Table 1):

TABLE 1

Complete feed for broilers

Composition in %

| | |
|---|---|
| Fishmeal | 6.0 |
| Feeding yeast | 2.0 |
| Soyabean oil | 4.35 |
| Coarse soyabean meal | 24.0 |
| Alfalfa meal | 1.0 |
| Corn | 44.615 |
| Wheat | 6.7 |
| Wheat middlings | 8.5 |
| Calcium phosphate for feeding | 1.4 |
| Calcium carbonate for feeding | 0.96 |
| Trace element mixture for poultry | 0.04 |
| Livestock salt | 0.09 |
| DL-methionine | 0.07 |
| Raiffeisen G1 vitamin premix | 0.015 |
| Choline chloride | 0.26 |
| | 100 |

The animals were kept in boxes of 40 animals each and were given the feed mixtures for 35 days in accordance with their group assignment. Weight change, feed intake and feed utilization are given in Table 2.

TABLE 2

Effect of the concentration of balhimycin in the feed on growth and feed utilization in broilers

| Group | Number n | Live weight Beginning g | End g | Gain g/day | Intake g/day | Feed Utilization kg of FI/kg of LW* |
|---|---|---|---|---|---|---|
| A | 152.00 | 41.3 | 1482.0 | 41.17c | 72.6 | 1.76 |
| Control | | | 139.8 | 3.95 | 4.12 | 0.03 |
| | | 100.0 | 100.0 | 100.0 | 100.0 | 100.0 |
| B | 151.00 | 40.0 | 1602.0 | 44.63b | 72.5 | 1.62*** |
| Balhimycin | | | 130.5 | 3.73 | 0.78 | 0.02 |
| 15 mg/kg | | 96.9 | 108.1 | 108.4 | 99.9 | 92.0 |
| C | 156.00 | 43.5 | 1640.0 | 45.62a | 75.3 | 1.65** |
| Balhimycin | | | 125.4 | 3.59 | 1.33 | 0.04 |
| 30 mg/kg | | 105.3 | 110.7 | 110.8 | 100.6 | 93.8 |
| D | 154.00 | 42.0 | 1617.0 | 44.99ab | 73.0 | 1.62*** |
| Balhimycin | | | 134.7 | 3.85 | 1.73 | 0.02 |
| 45 mg/kg | | 101.7 | 109.1 | 109.3 | 100.6 | 92.0 |
| E | 156.00 | 42.3 | 1600.0 | 44.50b | 73.1 | 1.64** |
| Balhimycin | | | 141.1 | 4.02 | 2.29 | 0.03 |
| 60 mg/kg | | 102.4 | 108.0 | 108.1 | 100.7 | 93.2 |

Feed utilization:
***$P < 0.001$
**$P < 0.005$, significant in comparison with the control
*kg of FI/kg of LW = kg of feed intake/kg of live weight gain In Table 2, the first number in each column directed to weight change, feed intake, and feed utilization, indicates the number average for the broilers in each group. The second number indicates the standard deviation of the data. The third number indicates the percent difference of each group as compared to the control value of 100%.

Different letters (a, b, ab, c) in the gain column denote significant differences between the groups ($P<0.05$). Values having the same letter or letters indicate that there is no significant difference between the groups.

We claim:

1. A method for promoting production in a monogastric or polygastric animal which comprises administering to said monogastric or polygastric animal an effective amount of balhimycin.

2. The method as claimed in claim 1 wherein the balhimycin is administered in combination with at least one derivative of balhimycin selected from the group consisting of desmethylbalhimycin, demethylleucylbalhimycin, deglucobalhimycin, methylbalhimycin, balhimycin R and balhimycin V and/or their hydrates and/or physiologically tolerated salts.

3. The method as claimed in claim 2, wherein the balhimycin is administered in a dose of from 0.1 to 600 mg of per kg of bodyweight per day.

4. The method as claimed in claim 1, wherein the balhimycin administered in a dose of from 0.1 to 600 mg per kg of bodyweight per day.

5. The method of claim 2, wherein balhimycin is administered together with solid or liquid complete feed, supplementary feed, or drinking water.

6. The method as claimed in claim 1, wherein the balhimycin is administered together with solid or liquid complete feed, supplementary feed, or drinking water.

7. The method as claimed in claim 2, wherein the balhimycin is administered a solid or liquid concentrate or premix.

8. The method as claimed in claim 1, wherein the balhimycin is administered as a solid or liquid concentrate or premix.

9. A pharmaceutical composition for promoting production in monogastric or polygastric animals, which comprises an effective amount of balhimycin together with a physiologically tolerated carrier.

10. The pharmaceutical composition as claimed in claim 9 wherein the balhimycin is present in combination with at least one derivative of balhimycin selected from the group consisting of desmethylbalhimycin, demethylleucylbalhimycin, deglucobalhimycin, methylbalhimycin, balhimycin R and balhimycin V and/or their hydrates and/or physiologically tolerated salts.

11. The pharmaceutical composition as claimed in claim 10, in the form of a tablet, a capsule, a paste, a granule composition, a powder, a juice, a syrup, a salt lick, a bolus or a slow-release bolus.

12. The pharmaceutical composition as claimed in claim 9, in the form of a tablet, a capsule, a paste, a granule composition, a powder, a juice, a syrup, a salt lick, a bolus or a slow-release bolus.

13. An implant for the parenteral administration of the pharmaceutical composition as claimed in claim 10, wherein the composition is released from the implant.

14. An implant for the parenteral administration of the pharmaceutical composition as claimed in claim 9, wherein the composition is released from the implant.

15. The pharmaceutical composition as claimed in claim 10, wherein the balhimycin is present in combination with one or more of derivatives of balhimycin together with non-volatile constituents in the culture broth of the balhimycin fermentation.

16. The pharmaceutical composition as claimed in claim 9, wherein the balhimycin is present in combination with non-volatile constituents in the culture broth of the balhimycin fermentation.

17. A method for promoting production in a monogastric or polygastric animal which comprises administering to said monogastric or polygastric animal a pharmaceutical composition as claimed in claim 10.

18. A method for promoting production in a monogastric or polygastric animal which comprises administering to said monogastric or polygastric animal a pharmaceutical composition as claimed in claim 9.

* * * * *